US012661031B2

(12) United States Patent
Zorn et al.

(10) Patent No.: US 12,661,031 B2
(45) Date of Patent: Jun. 23, 2026

(54) MEASURING APPARATUS

(71) Applicant: Ventilytics GmbH i. Gr., Heuchelheim (DE)

(72) Inventors: Alexander Zorn, Heuchelheim (DE); Steffen Fuchs, Lahnau (DE)

(73) Assignee: Ventilytics GmbH i. Gr., Heuchelheim (DE)

( * ) Notice: Subject to any disclaimer, the term of this patent is extended or adjusted under 35 U.S.C. 154(b) by 441 days.

(21) Appl. No.: 18/108,278

(22) Filed: Feb. 10, 2023

(65) Prior Publication Data

US 2023/0270351 A1 Aug. 31, 2023

(30) Foreign Application Priority Data

Feb. 25, 2022 (EP) ..................................... 22158801

(51) Int. Cl.
*A61B 5/083* (2006.01)
*G01N 33/497* (2006.01)
(52) U.S. Cl.
CPC ......... *A61B 5/0836* (2013.01); *G01N 33/497* (2013.01)
(58) Field of Classification Search
None
See application file for complete search history.

(56) References Cited

U.S. PATENT DOCUMENTS

| | | |
|---|---|---|
| 2002/0029003 A1 | 3/2002 | Mace et al. |
| 2016/0258920 A1 | 9/2016 | Nosovitskiy et al. |
| 2017/0184492 A1 | 6/2017 | Hong et al. |

| | | |
|---|---|---|
| 2018/0078175 A1 | 3/2018 | Patel et al. |
| 2018/0153440 A1 | 6/2018 | Lee et al. |
| 2019/0282124 A1 | 9/2019 | Wu et al. |
| 2020/0023297 A1 | 1/2020 | Disson et al. |
| 2020/0093399 A1* | 3/2020 | Miller .................... A61B 5/097 |
| 2020/0232971 A1 | 7/2020 | Hedrich et al. |
| 2021/0052192 A1 | 2/2021 | Ratto et al. |

FOREIGN PATENT DOCUMENTS

| | | |
|---|---|---|
| DE | 202009013577 U1 | 2/2010 |
| EP | 2745775 A1 | 6/2014 |
| KR | 20030009013 A | 1/2003 |

OTHER PUBLICATIONS

Extended European Search Report for corresponding European Patent Application No. EP 22158801 dated Oct. 3, 2022 (in German).

Partial European Search Report for corresponding European Patent Application No. EP 22158801 dated Aug. 3, 2022 (in German).

* cited by examiner

*Primary Examiner* — Jay B Shah
(74) *Attorney, Agent, or Firm* — HARNESS, DICKEY & PIERCE PLC

(57) ABSTRACT

A measuring device for determining the $CO_2$ content in the exhaled air of a living being, for example, a person or a mammal. The device may have a measuring tube defined by a wall, said measuring tube having an air inlet and an air outlet, with an inlet and an air outlet, with a $CO_2$ measuring device having a sensor pot which is in fluid communication with the measuring tube. The sensor pot extends through the wall of the measuring tube into the interior of the measuring tube, wherein the diameter of the measuring tube is reduced in the region of the sensor pot. The sensor pot is substantially open towards the measuring tube, such that the sensor pot is configured for direct measurement of the $CO_2$ content of air exhaled through the measuring tube, past the sensor pot.

15 Claims, 2 Drawing Sheets

MEASURING APPARATUS

CROSS-REFERENCE TO RELATED APPLICATIONS

This application claims priority to European Patent Application No. 22 158 801.5, filed Feb. 25, 2022. The entire disclosures of the above applications are incorporated herein by reference.

TECHNICAL FIELD

The invention relates to a measuring apparatus for determining the $CO_2$ content in the exhaled air of a living being such as a person or an animal. It has a measuring space, which is defined by a wall. It can substantially be the wall of a housing and a further partition. The measuring space further has an air inlet opening and an air outlet opening. For determining the $CO_2$ content there is provided a $CO_2$-measuring device, which is in fluidic communication with the measuring space. By way of this fluidic communication, a gas exchange between the $CO_2$-measuring device and the measuring space, in particular in respect of the exhaled air of the person, is possible, so that the $CO_2$ content in the exhaled air of the person can be measured and determined when the person exhales through the air inlet opening in the direction towards the air outlet opening.

BACKGROUND

Pulmonary hypertension refers to a disease in which the blood pressure in the pulmonary circulation is chronically high. It cannot readily be diagnosed because, for example, there are no blood tests with high sensitivity and sufficiently high specificity. At present, the probability of the diagnosis is estimated mainly by echocardiography and confirmed, if necessary, by means of right intracardiac catheter. However, this requires a high degree of specialization and knowledge of the person making the diagnosis.

Efforts are currently being made to determine the probability of the diagnosis at least with the assistance of the instantaneous $CO_2$ content in the exhaled air.

Measuring the $CO_2$ content in exhaled air is known and has long been routinely carried out, for example during anesthesia. However, the corresponding devices or units are relatively expensive and in most cases not mobile, because they are intended for stationary use during surgery.

In principle, a distinction is made in the case of $CO_2$-measuring devices between sidestream measurements and mainstream or instream measurements. In sidestream measurements, a portion of the stream is branched off from the actual airflow at a defined pressure, and the measurement is carried out on or in that portion. Very accurate measurements can here be achieved. However, the devices are very complex and the price thereof is therefore very high.

In a mainstream measurement, the measurement is carried out directly in the exhaled airstream. However, these measurements are erroneous owing to the different pressure profile on exhalation and exhibit deviations of up to 50%.

Mainstream measuring devices are known, for example, from US 2020/0232971 A1, US 2002/0029003 A1 or US 2018/0078175 A1. It is common to all those devices that they measure the $CO_2$ content in the exhaled air directly in one of the measuring tubes without branching. However, they have the disadvantage that this measurement principle yields significantly different measured values, so that an evaluation is very difficult.

Accordingly, an object of the invention is to provide a measuring apparatus for determining the CO2 content in the exhaled air of a living being, which apparatus is of simple construction and nevertheless has high measurement accuracy, and also a method for determining the CO2 content by means of such a measuring apparatus.

This object is achieved according to the invention by a measuring apparatus having the features of claim 1 and by a method for determining the $CO_2$ content in the exhaled air of a living being having the features of claim 10.

Preferred further developments and embodiments of the invention are indicated in the dependent claims, in the description and also in the figures and the explanation thereof.

The measuring apparatus according to the invention is developed further in that it has a sensor pot, which extends at least in part into the measuring space. It is here provided that the sensor pot extends through the wall of the measuring space into the interior of the measuring space, wherein the diameter or the clear width of the measuring space is reduced in the region of the sensor pot. The sensor pot is configured so as to be substantially open towards the measuring space. This means that exhaled air is able to enter the sensor pot. Furthermore, the $CO_2$-measuring device is arranged in the sensor pot and is configured to measure the $CO_2$ content of the air in the sensor pot directly.

The invention relates further to a method for determining the $CO_2$ content in the exhaled air of a living being, having a measuring apparatus according to the invention, wherein the living being exhales through the measuring space of the measuring apparatus multiple times.

The finding underlying the invention is that a major problem with measuring apparatuses of the type in question is that they produce inaccurate measurement results owing to the change in pressure that is present on exhalation. According to the invention, it has been recognized that the variation of the pressure can be reduced by providing a sensor pot which is open in the direction towards the measuring space and protrudes at least in part into the measuring space. Surprisingly, the pressure conditions on exhalation through the measuring space are significantly more constant within the sensor pot than within the remainder of the measuring space.

A further fundamental idea of the invention is that the sensor pot is configured so as to be substantially open towards the measuring space. This can mean, for example, that there is no reduction in the diameter or in the opening diameter of the sensor pot towards the measuring space. However, it can also be provided that a filter which has a very good airflow, that is to say a low air resistance, is provided in or at the upper end of the sensor pot in order to protect the $CO_2$-measuring device from bacteria or contamination.

The living being can be both a human being and an animal, in particular a mammal, for example a horse.

The sensor pot or measuring pot itself can be substantially cylindrical in shape, wherein one end face is in the form of an opening. It is preferred if the measuring space has a constant diameter over its entire length from the air inlet opening to an air outlet opening. This diameter is reduced in one region by the sensor pot. Reducing the diameter results in air turbulence in that region, so that it is ensured that the gas in the sensor pot substantially corresponds to the instantaneous exhaled air. High measurement accuracy is thereby achieved.

Advantageously, the ratio of the volume of the measuring space, disregarding the sensor pot, to the volume of the sensor pot is in the range of from 7:1 to 13:1. Ideally, it is in the region of 10:1. By means of this ratio it is achieved, surprisingly, that a relative constant pressure is present in the sensor pot during exhalation through the measuring space, so that a highly accurate measurement of the $CO_2$ content present in the gas can be carried out.

It is preferred if the air inlet opening and the air outlet opening are provided at opposite ends of the measuring space, and their prolongation forms a substantially straight virtual measuring tube. In other words, it is preferred if the air inlet opening and the air outlet opening have approximately the same diameter or the same opening area and are placed in a straight position relative to one another. A virtual measuring tube with a constant diameter can thus be formed through the measuring space.

In principle, the sensor pot can protrude into the measuring space or into the virtual measuring tube by any desired distance. However, it is preferred if the sensor pot is configured so as to protrude into the measuring space by up to at least one third of the diameter and not more than two thirds of the diameter of the virtual measuring tube. It is preferred if the sensor pot occupies approximately half of the diameter of the virtual measuring tube. In other words, the sensor pot, which protrudes into the virtual measuring tube, reduces the diameter of the virtual measuring tube in that region by between one third and two thirds. This dimensioning on the one hand ensures a good supply of fresh air to the sensor pot itself, and on the other hand a relatively constant pressure in the sensor pot is thus also achieved.

The high measurement accuracy can be improved further if the sensor pot is formed substantially perpendicular to a longitudinal axis of the measuring space and/or of the virtual measuring tube. In other words, the opening of the sensor pot is parallel to a plane which runs through the axis of rotation of the virtual measuring tube. In principle, tilting in the direction towards the air inlet opening or the air outlet opening is also possible, but a better measurement result is obtained with a dimensioning that does not implement this.

Different sensors can generally be provided in the $CO_2$-measuring device. However, preference is given according to the invention to an infrared-based sensor, because such a sensor can, for example, carry out its measurement over the entire interior of the sensor pot.

It has been found to be advantageous for the measurement accuracy if the $CO_2$-measuring device is configured to carry out a continuous measurement. Thus, a plurality of measured values can be determined during exhalation and can subsequently be processed further. However, a discontinuous measurement, which is carried out at short intervals, is in principle also possible.

Apart from the sensor pot, the interior of the measuring space can preferably be configured so that the air is able to flow from the air inlet opening to the air outlet opening substantially with little turbulence or even without turbulence. This in turn leads to a better airflow, so that the pressure which is established in the sensor pot is sufficiently constant. Generally, however, it is also possible to provide deflecting elements, but these require accurate positioning and dimensioning. By means of the proposed construction of a substantially low-turbulence air guide, the construction as a whole is facilitated. Therefore, the measuring space is designed preferably substantially straight, wherein a slight bend would in principle also be possible. To that end, the measuring space can have, for example, a U-like or U-shaped cross section.

The invention relates further to a method for determining the $CO_2$ content in the exhaled air of a living being, having a measuring device according to the invention. It is here provided that the living being exhales through the measuring space multiple times. During this exhalation, measurements can be carried out by means of the $CO_2$-measuring device of the measuring apparatus according to the invention.

It is preferred if the living being is prevented from exhaling through the nose in parallel. This can be achieved, for example, by a nose clip or by holding the nose.

It is preferred if the $CO_2$-measuring device carries out a continuous measurement of the $CO_2$ content in the exhaled air or of the gas within the sensor pot. In this manner, the optimal time at which the $CO_2$ measurement yields a result suitable for further processing can be determined.

Multiple, at least 7, preferably more than 9, maximum values determined by the $CO_2$-measuring device within a time range can be stored. The time range can be, for example, an exhalation process. A maximum value can be the highest value within a measuring period. It can be provided, for example, that the $CO_2$ content of the air or of the gas in the sensor pot is measured continuously during exhalation. Said content initially increases then falls again as soon as exhalation ends. Such a local maximum can also be used as the maximum value. The highest $CO_2$ value present in an exhalation, for example, can thus be determined.

In order to increase the evaluation accuracy further, a certain number of values from a group of maximum values—for example 2 or 3 of the lowest maximum values—can be disregarded in the final evaluation. In this way, erroneous measurements or measurements with low measurement accuracy can easily be filtered out.

It is preferred if there is outputted as the output value of the measured $CO_2$ a mean, in particular an arithmetic mean, or a maximum value. These values can also be adjusted before the corresponding mean is calculated.

It can further be provided that the measured values determined by the $CO_2$-measuring device are provided with a correction factor in order to take account of construction-related deviations, which are constant.

BRIEF DESCRIPTION OF DRAWINGS

The invention will be explained in detail hereinbelow with reference to an exemplary embodiment and schematic drawings, in which show.

DETAILED DESCRIPTION

Figure 2:
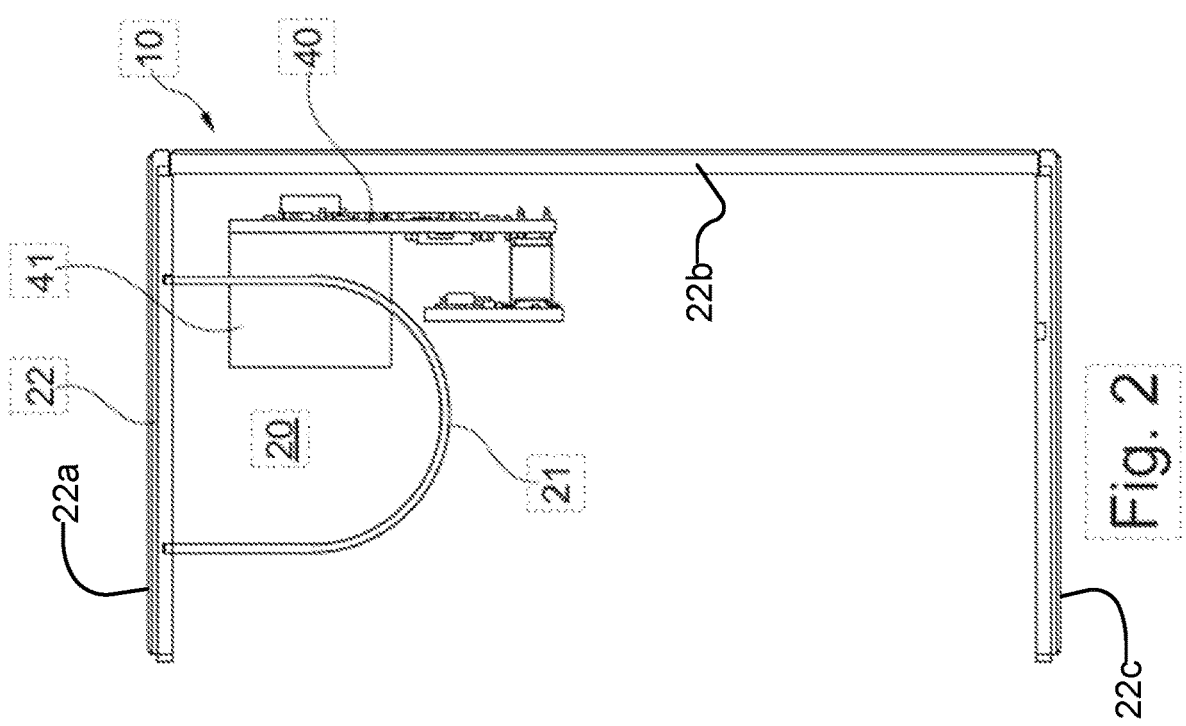
FIG. 2 a side view of the measuring apparatus according to the invention with some of the sides removed.
Figure 1:
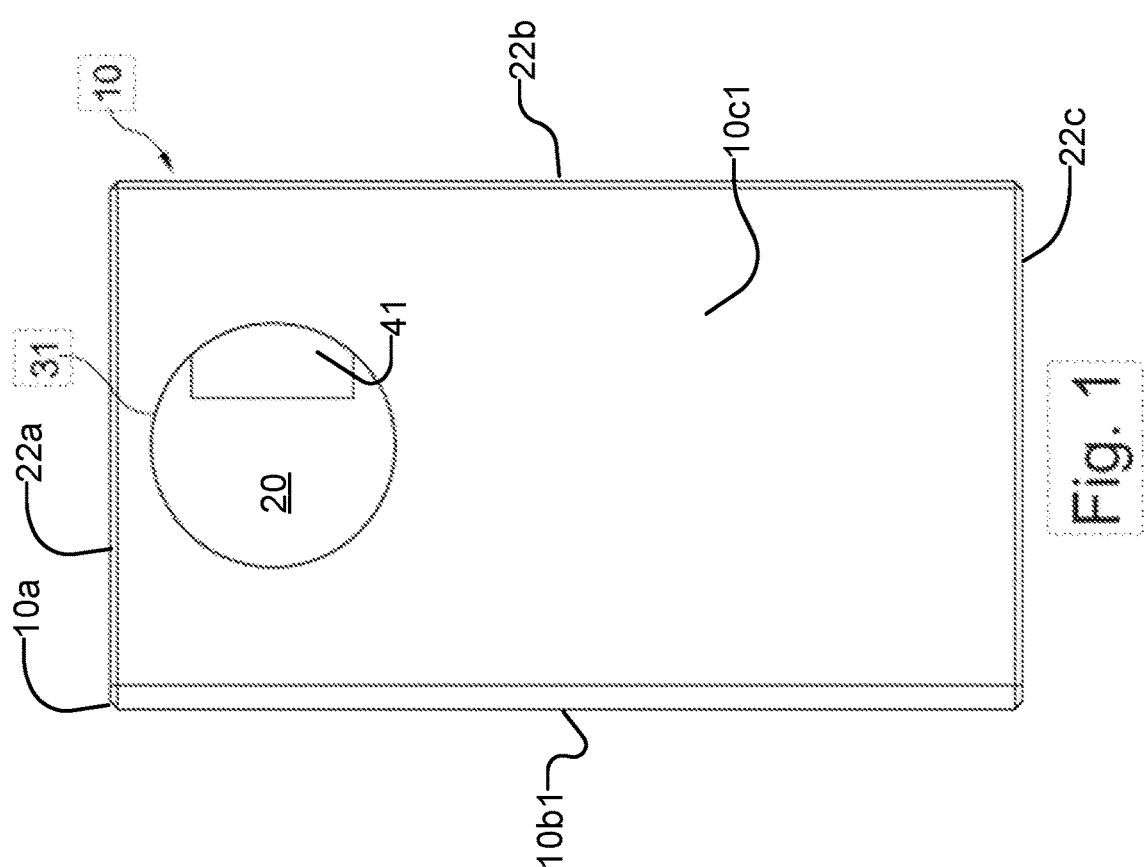
FIG. 1 a side view of a measuring apparatus according to the invention.

A measuring apparatus 10 according to the invention will be explained in detail hereinbelow on the basis of the figures. FIG. 1 shows a side view of a measuring apparatus 10 according to the invention. FIG. 2 shows the same view of the measuring apparatus 10 according to the invention, wherein a housing 10a has three side walls 10a1, 10b1 and 10c1 (visible in FIGS. 3-5), which have been removed so that the interior is visible. FIGS. 3 and 4 are each views, slightly in perspective, from different sides of the measuring apparatus 10 according to the invention. Finally, FIG. 5 shows the measuring apparatus 10 according to FIG. 4, wherein the three sides 10$a$1, 10$b$1 and 10$c$1 have again been removed so that part of the interior of the measuring apparatus 10 is visible.

The measuring apparatus 10 shown here has a substantially cuboidal housing 10$a$. However, the invention is not limited to this shape of housing. An air inlet opening 31 and an air outlet opening 32 are further provided in the walls 10$a$1 and 10$c$1, respectively. During use of the measuring apparatus 10, exhalation is carried out through the air inlet opening 31 through a measuring space, which is also referred to as a measuring chamber 20. In principle, the air inlet opening 31 and the air outlet opening 32 can also be inverted.

Figures 3, 4, 5:
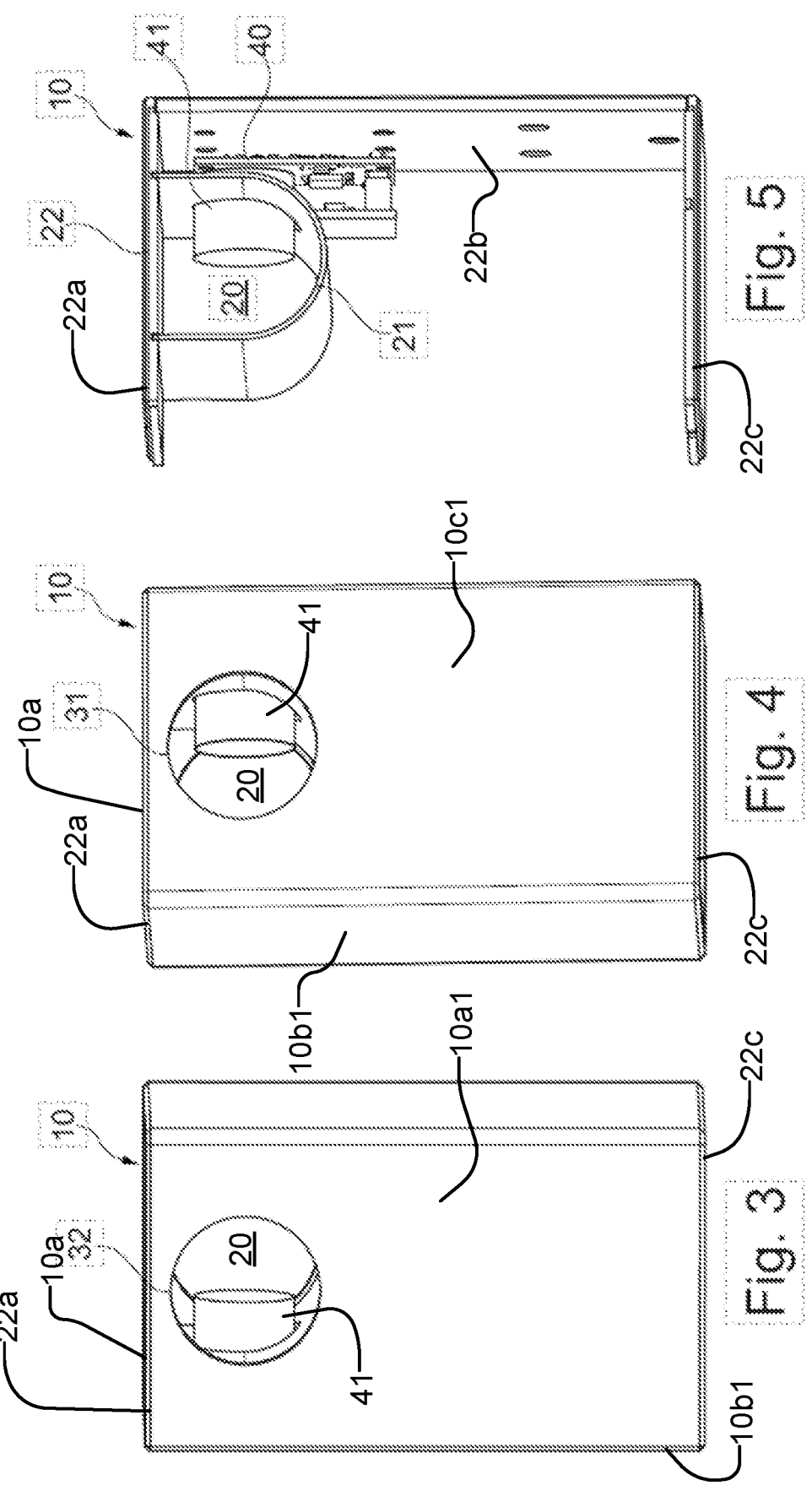
FIGS. 3 and 4 two perspective side views of the measuring apparatus according to the invention.
FIG. 5 the measuring apparatus according to the invention of FIG. 4 with some of the sides removed.

The measuring chamber 20 is shown in particular in FIGS. 4 and 5. It is formed by a U-shaped wall 21 and an upper portion 22$a$ of the outer wall 22. The outer wall 22 also includes portions 22$b$ and 22$c$. As is apparent from FIGS. 1, 3 and 4, the air inlet opening 31 and the air outlet opening 32, which in this embodiment are formed circular, lead to the measuring space 20. Other opening cross sections are possible, however. The openings, as is apparent in particular from FIG. 1, are preferably formed exactly opposite one another, so that their prolongation forms a virtual measuring tube.

A $CO_2$-measuring device 40 extends into the measuring space 20. Said device has a sensor pot 41, which protrudes into the measuring space 20. In the sensor pot 41 there is a $CO_2$-measuring device 40, which measures the $CO_2$ in the sensor pot 41 by means of infrared measurement, for example. The sensor pot 41 is preferably equidistant from the air inlet opening 31 and the air outlet opening 32 and is located in the middle between them.

The sensor pot 41 is in fluidic communication with the measuring space 20. It can simply be designed openly. However, it is preferred if the sensor pot 41 has a filter or a membrane so as to prevent contamination of the interior of the sensor pot 41. It is important here that said filter or membrane has good air permeability.

As is apparent in particular from FIG. 1, the sensor pot 41 of the $CO_2$-measuring device 40 protrudes into the virtual measuring tube which is formed between the air inlet opening 31 and the air outlet opening 32.

According to the invention, it has been recognized that, on exhalation through the air inlet opening 31, a relatively constant pressure is established within the sensor pot 41, so that the measurement present there unexpectedly has a very high accuracy.

The invention claimed is:

1. A measuring apparatus for determining a $CO_2$ content in the exhaled air of a living being including at least one of a person or a mammal, the apparatus comprising:

a housing defining an air inlet opening and an air outlet opening;

a wall disposed within the housing forming a virtual tube, and defining a measuring space within the virtual tube, wherein the measuring space is in communication with, and extends between, the air inlet opening and the air outlet opening;

a $CO_2$-measuring device projecting laterally relative to the virtual tube, and which is in fluidic communication with the measuring space within the virtual tube, the $CO_2$measuring device including a sensor pot; wherein

6 the sensor pot extends at least in part through the wall of the virtual tube into the measuring space within an interior area of the virtual tube, wherein a diameter of the measuring space is reduced in a region of the sensor pot;

the sensor pot is configured so as to be open towards the measuring space; and the $CO_2$-measuring device is arranged in the sensor pot and is configured to measure the $CO_2$ content of the air in the sensor pot directly.

2. The measuring apparatus according to claim 1, wherein the measuring space has a constant diameter over its entire length from the air inlet opening to the air outlet opening, except for a region where the diameter of the measuring space is reduced.

3. The measuring apparatus according to claim 1, wherein the ratio of a volume of the measuring space, disregarding the sensor pot, to a volume of the sensor pot is in the range of from 7:1 to 13:1.

4. The measuring apparatus according to claim 1, wherein the air inlet opening and the air outlet form opposite ends of the measuring space, and their prolongation configures the virtual tube as a straight virtual measuring tube.

5. The measuring apparatus according to claim 4, wherein the sensor pot is arranged substantially perpendicular to a longitudinal axis of the straight virtual measuring tube.

6. The measuring apparatus according to claim 1, wherein an infrared-based sensor is provided in the $CO_2$-measuring device.

7. The measuring apparatus according to claim 1, wherein the $CO_2$-measuring device is configured to carry out a continuous measurement.

8. The measuring apparatus according to claim 1, wherein the interior of the measuring space is configured such that air, apart from the sensor pot, is able to flow from the air inlet opening to the air outlet opening substantially without turbulence.

9. The measuring apparatus according to claim 1, wherein the measuring space has a U-shaped cross section.

10. A method for determining the $CO_2$ content in the exhaled air of a living being, having a measuring apparatus according to claim 1, wherein the living being exhales into the air inlet opening through the measuring space multiple times.

11. The method according to claim 10, wherein the $CO_2$-measuring device carries out a continuous measurement of the $CO_2$ content.

12. The method according to claim 10, wherein at least 7 maximum values determined by the $CO_2$-measuring device are stored.

13. The method according to claim 10, wherein at least the two lowest maximum values of a plurality of maximum values are disregarded in the final evaluation.

14. The method according to any claim 10, wherein there is outputted as the output value a mean, in particular an arithmetic mean, of a plurality of maximum values.

15. The method according to claim 10, wherein the measured values determined by the $CO_2$-measuring device are provided with a correction factor.

* * * * *